United States Patent [19]

Scott et al.

[11] Patent Number: 4,950,222
[45] Date of Patent: Aug. 21, 1990

[54] ISOLATOR FOR USE IN SURGERY OR AS A CLEAN ROOM AND METHOD OF USING THE SAME

[75] Inventors: Frank B. Scott; Charley J. Fields; James M. Fowler, Jr., all of Houston, Tex.

[73] Assignee: Lone Star Medical Products, Inc., Houston, Tex.

[21] Appl. No.: 251,072

[22] Filed: Sep. 28, 1988

Related U.S. Application Data

[63] Continuation of Ser. No. 75,249, Jul. 16, 1987, abandoned, which is a continuation of Ser. No. 726,088, Apr. 23, 1985, abandoned, which is a continuation-in-part of Ser. No. 676,204, Nov. 28, 1984, abandoned, which is a continuation of Ser. No. 485,210, Apr. 15, 1983, abandoned.

[51] Int. Cl.$^5$ .............................................. A61G 13/00
[52] U.S. Cl. ............................................ 600/21; 312/1
[58] Field of Search ...................... 600/21; 128/205.26; 312/1, 3, 209

[56] References Cited

U.S. PATENT DOCUMENTS

| | | | |
|---|---|---|---|
| 2,473,033 | 6/1949 | Letac | 600/21 |
| 3,265,059 | 8/1966 | Matthews | 600/21 |
| 3,272,199 | 9/1968 | Matthews | 600/21 |
| 3,850,172 | 11/1974 | Cazalis | 128/204 |
| 3,907,389 | 9/1975 | Cox et al. | 128/1 R X |
| 4,026,286 | 5/1977 | Trexler | 128/205.26 |
| 4,161,172 | 7/1979 | Pickering | 128/205.26 X |
| 4,275,719 | 6/1981 | Mayer | 128/1 R X |
| 4,328,793 | 5/1982 | Martin | 128/205.26 X |
| 4,367,728 | 1/1983 | Mutku | 128/205.26 X |
| 4,550,713 | 11/1985 | Hyman | 600/21 |

OTHER PUBLICATIONS

Roche Medical Image, "Germ-Free Research Vistas", pp. 27–29, Autumn, 1981.

*Primary Examiner*—William E. Kamm
*Attorney, Agent, or Firm*—Vaden, Eickenroht, Thompson & Boulware

[57] ABSTRACT

An isolator and method of using it for providing a contamination-free atmosphere in which a surgical procedure can be performed or equipment that is sensitive to environmental contamination can be assembled. The isolator includes an inflatable bag of flexible material through which filtered air is circulated. For use in surgery, a portion of the lower side is made of an elastic surgical drape material to allow a body member upon which a surgical procedure is to be performed to be pulled into the work space of the bag. A portion of the top side of the bag is made of a relatively stiff, optically transparent, material through which the surgeon or the assembly worker can view the work area. A plurality of open-ended sleeves are attached to the bag through which the hands and arms of the surgeon and his assistants or the worker can extend into the work space.

18 Claims, 3 Drawing Sheets

ISOLATOR FOR USE IN SURGERY OR AS A CLEAN ROOM AND METHOD OF USING THE SAME

This application is a continuation of application Ser. No. 07/075,249, filed July 16, 1987, entitled "Isolator for Use in Surgery or as a Clean Room and Method of Using the Same", now abandoned, which was a continuation of application Ser. No. 726,088, filed Apr. 23, 1985, now abandoned, which was a continuation-in-part of application Ser. No. 676,204, filed Nov. 28, 1984, entitled "Surgical Isolator", now abandoned, which was a continuation of Ser. No. 485,210, filed Apr. 15, 1983, entitled "Surgical Isolator", now abandoned.

This invention relates to an isolator for providing a contaminant-free atmosphere in which a surgical procedure can be performed or equipment sensitive to environmental contamination can be assembled and to a method of using the same.

A large amount of effort is spent in the avoidance of contamination of surgical wounds by disease organisms in the operating room. All instruments and dry goods coming into contact with the surgical field are sterilized, either in an autoclave or with chemicals. Chemicals are used to sterilize the patient's skin in the area of the surgery. The surgical team scrub their hands and arms for at least five minutes after which hands and arms are bathed in alcohol. Sterilized gowns, caps, and masks that filter the team's exhaled air are worn by the surgical team along with sterile gloves that cover their hands. Thereafter, the surgical team avoids contact with non-sterilized objects. Further, the air in the operating room is constantly changed and filtered.

Even with all this preparation and attention to sterilization, a significant percentage of supposedly clean operations result in wound infections, which means that operating aseptically on man remains only a concept and not an accomplished procedure.

One of the problems is that disease organisms are ubiquitous in operating room air, on the patient's skin, in his gastrointestinal tract, and in the exhalations of all persons in the room. Also, the individuals of the surgical team shed disease organisms as they move around the operating room during the surgery For example, it has been determined that 30,000 to 60,000 particles are shed each minute from each person in the operating room. Foreign particles that have been shown to cause granuloma, a type of infection, include lint, wood fibers, talc dust and related agents. These particles come from drapes, gloves, wrapping materials and other items found inside the operating room (OR). Bacterial contaminants are released into the atmosphere from the skin and hair, by breathing and passing gas, and from the urinary tracts of the surgical team and the patient.

There are certain types of surgery that experience a higher than normal rate of infection. It is these surgeries where the use of the isolator of this invention is most important. Surgeries involving the implantation of a prosthetic device or artificial organ is a common example. The dose of bacteria necessary to invade the wound and cause an infection is reduced when foreign matter, such as an implanted device, is introduced into the body. Repeated experimental and clinical studies have proven that the mere presence of a foreign body can seriously impede the human body's immune system. Over 50,000 bacteria may be required to cause a surgical wound infection in normal operations whereas only 100 bacteria can cause infection when an implant device, even though inert, is introduced. In some implant surgeries, it has been theorized that a single bacterium may be all that is necessary to cause a deep wound infection.

Certainly many wound infections can be attributed to endogenous (patient) causes It is generally agreed, though, that airborne contamination during surgery contributes in some degree to the number of infections. Indeed, there is much empirical evidence and many major comprehensive studies that suggest it as the prime contributor. The complications that develop from wound infection can be very serious and it is a continuing problem that plagues the operating community as well as the patient The isolator of this invention will provide surgeons and patients with an extra preventative measure against surgical wound infections.

Therefore, it is an object of this invention to provide an isolator and a method of using the isolator that includes a tent or bag of flexible, impervious material for placing on the area of the patient where the surgery is to be done and pumping a continuous stream of filtered air that flows from one side of the bag across the surgical wound to exhaust ports on the opposite side of the bag to maintain the bag inflated at a pressure above atmospheric and to constantly change the air in the isolator.

It is a further object of this invention to provide such an isolator and a method of using the isolator where the instruments and other material used during the surgery is moved into and out of the bag through a door in the side where the exhaust ports are located so the air is always moving in a direction to keep any contaminants outside the bag from entering the bag while the door is open.

It is a further object to provide such an isolator and method in which the instruments and other material are moved into and out of the bag through an air lock, the doors of which have exhaust ports through which most of the air flows to the outside.

It is a further object and feature of this invention to provide an isolator having an air lock that can be severed from the isolator when the surgery is completed to protect the instruments that have been used during the surgery from the air in the operating room so the instruments will be readily available, if needed, during the period between the completion of the surgery and the moving of the patient from the operating room.

The first surgical isolators were developed for use in gnotobiotics where germ-free laboratory animals were obtained by delivering such animals from their parents by Caesarean section directly into an aseptic environment. Later a plastic isolator for use on humans was designed by Levenson, et al and described in an article entitled "A Plastic Isolator for Operating in a Sterile Environment" American Journal of Surgery, 104, 891–899, 1962. A subsequent isolator was developed by McLauchlan, et al and described in an article entitled "The Surgical Isolator", British Medical Journal, 1(903): 322–4, 23 Feb., 1974. Both of these isolators are discussed in "Air Contamination Control in Hospitals" by Joseph R. Luciano, Copyright 1977, Plenum Press, New York, pages 355–359.

Both the Levenson and McLauchlan isolators included bags of thin, flexible, plastic material inflated with sterile air. Both have jackets or sleeves that extend into the bag and that cover the surgeon and his assistant's arms during the surgery. The jackets and sleeves are closed at their ends by the gloves that the surgeons wear. This makes it very difficult for the surgeons to change gloves during the surgery should one of the gloves tear. Also, should it be necessary to remove the isolator and complete the surgery without it, the surgeon would have to be regloved before he could proceed. Another disadvantage of this arrangement, is that since the gloves are attached to their ends, the sleeves or jackets extend into the work area of the isolator to the same extent as the arms of the surgical team and tends to partially obscure the vision of the surgeon, as well as just being somewhat in the way of the surgical team as it works.

It is therefore an object of this invention to provide an isolator having sleeves through which the surgical team can extend their pregloved hands and arms into the work space with the open end of the sleeves engaging their arms above the elbow and held in place by elastic so that the sleeves fold in upon themselves or intussuscept as required to allow the arm to which it is attached to move freely into and out of the bag and into and out of the work space of the isolator above the surgical wound of the patient.

The isolators of both Levenson and McLauchlan had clear plastic in the top through which the surgical team could view the surgical field, but the plastic was flexible and would change shapes depending upon the air pressure in the isolator and would tend to balloon away from the surgical field.

Therefore, it is an object of this invention to provide an isolator comprising an inflatable bag having side and end walls of flexible material and an upper side, a portion of which is of flexible material and a portion of which is of a relatively stiff, optically transparent material, that is designed so that when the bag is inflated, it will assume a position a predetermined distance above the surgical field and remain substantially in that position throughout the operation giving the surgeon and assistants a clear and unlimited view of the surgical field and ample room inside the bag in which to work.

It is another object of this invention to provide a surgical isolator comprising an inflatable bag of flexible material that is impervious to disease organisms that includes a section in the upper wall of relatively stiff, optically transparent, material that will assume a position when the bag is inflated that is substantially straight along the longitudinal axis of the bag and slightly convex or V-shaped along the transverse axis of the bag to provide a window through which the surgeon has a clear view of the surgical field.

It is a further object of this invention to provide an improved arrangement for filtering the air being pumped into the bag to decrease the possibility of contaminating the sterile isolator when the bag is connected to the blower supplying the air to the bag.

It is a further object of this invention to provide a blower-air filter assembly for providing filtered air under pressure to the bag of the isolator in which any leakage will be of filtered air back to the suction side of the blower to keep non-filtered air from entering the bag.

It is a further object of this invention to provide an isolator having a bag that is inflated with sterile air from a blower-filter assembly that passes through another filter located in the sterile air duct between the blower-filter assembly and the bag so that the connection between the sterile air duct and the blower-filter assembly is made upstream from this filter to entrap any contaminants that are introduced into the air duct when the connection is made.

It is a further object of this invention to provide an isolator comprising an inflatable bag of flexible material a portion of the lower side of which is made of an elastic material through which a body member upon which a surgical procedure is to be performed, can be pulled into the work space in the bag through an incision in the elastic material that is smaller than the member to cause the stretched elastic material to tightly surround the member and isolate the body member from the environment outside the work space.

The objects and advantages of the isolator of this invention in solving the problem of infections in surgical procedures have been described above. The isolator of this invention also has utility in industry. It can replace the "clean rooms" now used to provide a contamination-free atmosphere in which equipment is assembled that is especially sensitive to environmental contamination, such as dust. A typical clean room has an atmospheric-control system that rigidly controls temperature and humidity and bars entrance, by means of filters, of all but the tiniest mote of dust. Walls and ceilings are of one-piece plastic with no cracks where dust might collect and are washed and vacuumed daily. Maintenance cannot be done within the room: plumbing, wiring, and lighting are so arranged that maintenance can be handled in crawl spaces above the ceiling. The room has no sharp corners; they are rounded off to forestall dust collection.

Before entering, workers don special clean suits, including head covering and boots, and pass under an "air shower" that removes all loose particles of matter. The parts that make up the assembly are thoroughly cleaned and polished before delivery to the clean room, which they enter through an air lock.

With the isolator of this invention, much of the elaborate equipment, special room design, and special clean suits can be eliminated greatly reducing the cost of a clean room operation.

These and other objects, advantages, and features of this invention will be apparent to those skilled in the art from a consideration of this specification, including the attached drawings and appended claims.

Figure 1:
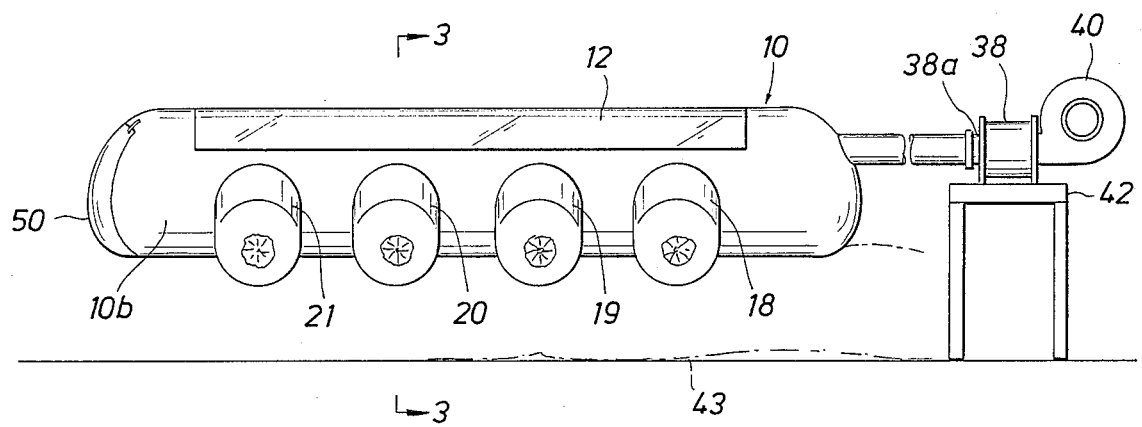
FIG. 1 is a side view, in elevation, of one embodiment of the isolator of this invention inflated and in position on a patient shown in dotted lines.

The isolator shown in the drawings is described below as it is used in a surgical procedure. As explained above, it can be used as a clean room for industrial purposes equally as well.

The isolator shown in FIGS. 1-5 and generally indicated by the number 10, is essentially a bag that is inflated in use. It is made of materials through which disease organisms cannot pass. Most of the bag, in the preferred embodiment, is made of a clear, flexible acrylic resin plastic except for optical window 12 in the top portion of the isolator and a portion of the bottom side of the isolator, where a special material is provided for certain surgical procedures that will be described below.

Window 12 is made out of a relatively stiff, optically clear, plastic material, such as the thermoplastic carbonate-linked polymer produced by reacting bisphenol A and phosgene and sold under the trademark "Lexan" by the General Electric Co. It provides the surgical team with a clear, undistorted, view of the surgical field. In addition, the window, being relatively stiff compared to the acrylic material used for the rest of the bag, will cause the inflated bag to assume a more or less elliptical shape in cross-section as shown in FIG. 3. In the embodiment shown in FIGS. 1-5, the window is substantially straight along the longitudinal axis of the bag and slightly convex along the transverse axis. It is also a stable window that will assume a position relative to the bottom of the bag and substantially maintain that position even though the pressure in the bag may change slightly during the time it is in use. Further, it will not undulate or balloon under the pressure, which could distort the view through the window.

Figure 5:
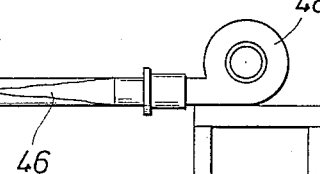
FIG. 5 is a side view, in elevation, of the isolator showing an alternate arrangement for positioning the filter used to filter the air entering the isolator.

Side walls 10a and 10b of the isolator are provided with openings that connect to open ended sleeves 14-21 attached to the side wall of the isolator. In this embodiment, four sleeves are provided on each side of the isolator. The sleeves are open ended, but are held substantially closed, when not in use, by rubberized elastic attached to the sleeves adjacent the ends. In use, the surgeon will extend his arms through the openings in, for example, sleeves 14 and 15, as they are held open by an assistant, until the elastic band of the sleeves is somewhere above his elbow. Then as the surgeon extends his arms into the working space between the bottom of the isolator and window 12, the sleeves will turn inwardly on themselves or intussuscept as required to allow the arms to which they are attached to move freely into the isolator. In FIG. 5, for example, the surgeon has his arms sufficiently inside the isolator to perform his surgery, yet sleeves 14 and 15 are outside of the working space of the isolator so as not to interfere with the movement of the surgeon's hands or arms or interfere with his vision of the surgical field.

In this arrangement, the surgeon is gloved outside the isolator. If he needs to change gloves during the surgery, he can simply pull his arms out of sleeves 14 and 15, be regloved, and reinsert his hands and arms back into the isolator through sleeves 14 and 16. This can be done quickly and easily.

Further, if for some reason, it is necessary to remove the isolator before the surgery is completed, the surgeon can remove his arms from the sleeves, remove the isolator, and immediately continue without having to be regloved as is the case with the prior art isolators. Some air leaks out through sleeves 14 and 15 both when the surgeon has his arms in the sleeves and also when they are not in use. This positive flow of air along the sleeves of the surgeon and out through the opening end of the sleeves through which the surgeon's arms extend, prevents disease organisms from the surgeon from entering the isolator to contaminate and infect the surgical wound.

It is another advantage and feature of this invention to make a portion of the bottom of the isolator out of a surgical drape of resilient material. This allows a body member, upon which a surgical procedure is to be performed, to be pulled into the work space of the isolator through an incision in the drape that is smaller than the body member. The stretched elastic material tightly engages the member to reduce the chances of disease organisms from entering the work space from the outside. Any air that leaks through the opening in the drape will tend to carry such organisms away from the work space. This feature, of course, is advantageous where the body member is of such shape and size that it can be pulled into the work space conveniently so as to isolate it from the outside environment and from the body of the patient itself. For example, a foot, a knee, a whole leg, or a portion thereof, hands, arms, head, and genitalia are examples of body members that could be so handled.

Figure 2:
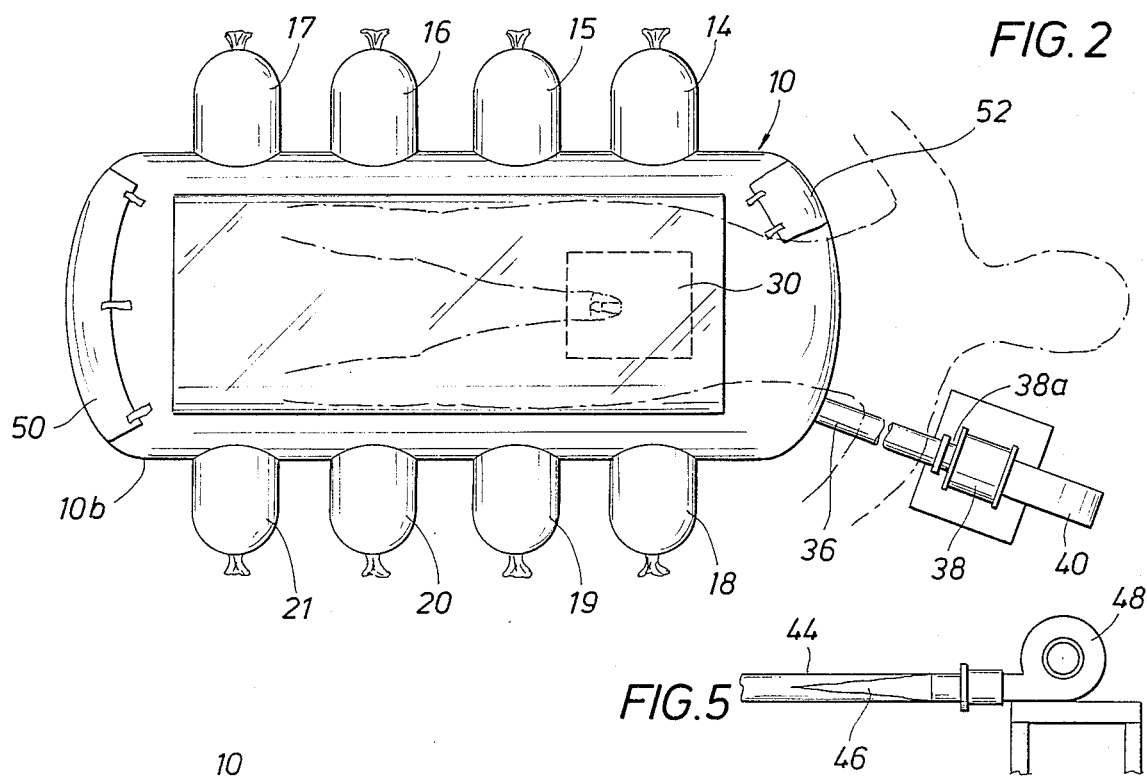
FIG. 2 is a top view of the isolator of FIG. 1.
Figure 3:
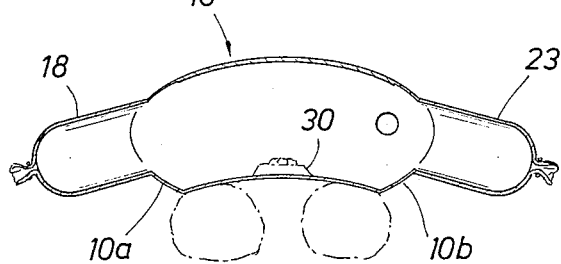
FIG. 3 is a sectional view taken along line 3-3 of FIG. 1.

In FIG. 2, drape portion 30 is positioned so that the patient's genitalia can be pulled through an incision in the drape and isolated from the outside during a surgical procedure, such as the implantation of a penile prosthesis.

Air conduit 36 is integrally attached to the isolator and sterilized along with the isolator before it is placed in use. In the operation room, the end of conduit 36 is attached to filter 38 connected to the outlet of blower 40. Filter 38 is of the type that will filter out disease organisms to prevent them from entering the isolator. The filter and blower are supported on table 42 located adjacent operating table 43.

In most cases, the outlet side of filter 38 will not be as sterile as is desired for use with the isolator. Even if sterile, someone has to make a connection between conduit 36 and the outlet of the filter and this can introduce disease organisms into the conduit when the connection is being made. The connection usually consists of slipping the end of conduit 36 over outlet to 38a and clamping or taping the conduit in place.

Figure 4:
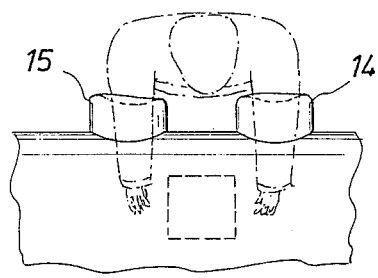
FIG. 4 is a top view of a surgeon with his arms extending through two of the sleeves of the isolator showing the intussusceptive action of the sleeves as the surgeon's arms move into the isolator.

It is another feature and advantage of this invention to provide conduit 44 that has conical filter 46 installed in the conduit downstream from its end, as shown in FIG. 5. Filter 46 will prevent any disease organisms that are introduced into the conduit, while it is being connected to the blower, from reaching the isolator Filter 38, described above, is classified as a high efficiency particle air (HEPA) filter. Conically shaped filter 46, in the embodiment shown in FIG. 4, is made of thin plastic membrane like material having a porosity of several million pores per square inch that can filter bacteria out of the moving air stream. One such material is marketed by E.I. duPont de Nemours & Co. under the trademark "REMAY", Style 2016, and is made of a spun bound polyester.

One end wall of the isolator includes rather large flap 50 that is held in the closed position by tape. Instruments and the like are moved into and out of the isolator through this flap. Suction tubes, cautery, and the like can be inserted through smaller flap 52 at the other end. Air continuously leaks out of the isolator through the flaps and the sleeves. This is desirable since there should be a continuous flow of sterile air over the surgical wound, not a blast of air, of course, but steady movement. The elastic holding the sleeves closed can function to regulate pressure in the isolator. As it increases, it will open the sleeves letting out more air and vice versa.

Figure 6:
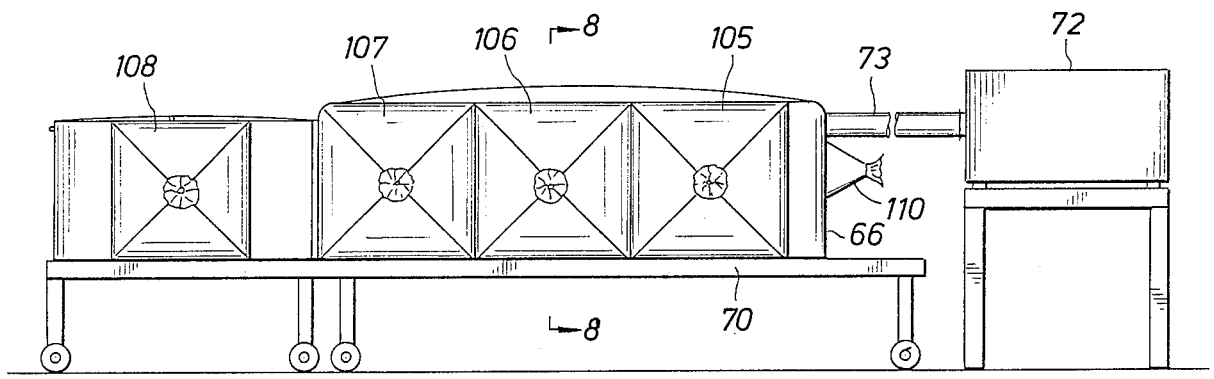
FIG. 6 is a side view in elevation of an alternate embodiment of the isolator of this invention.
Figure 7:
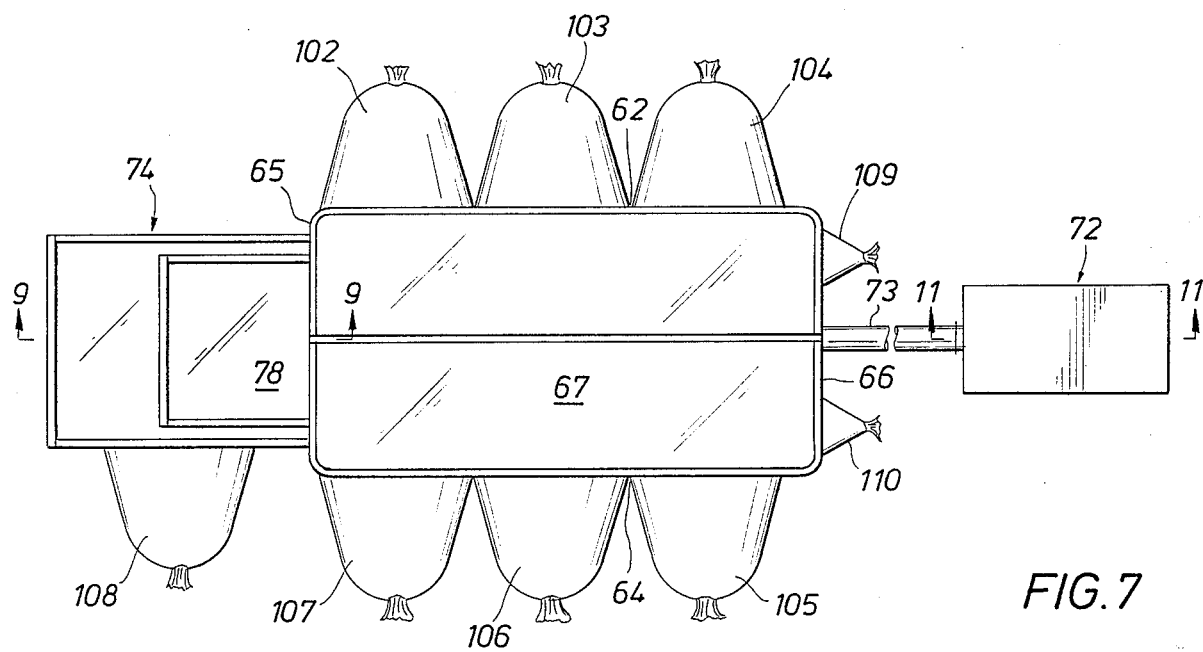
FIG. 7 is a plan view of the isolator of FIG. 6.
Figure 8:
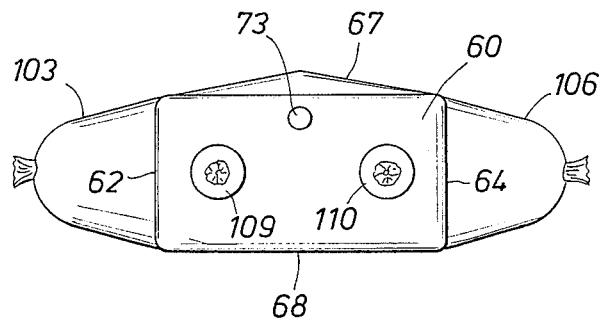
FIG. 8 is a sectional view taken along line 8—8 of FIG. 6.

An alternate embodiment of the surgical isolation system of this invention is shown in FIGS. 6-11. It includes inflatable bag or bubble 60, which is generally rectangular in cross-section, having side walls 62 and 64, end walls 65 and 66, top 67, and bottom 68. The bag in FIG. 6 is shown inflated and resting on operating table 70. There is a patient between the bag and the operating table, but for the sake of clarity, the patient is not shown. It is understood that the bag is resting on top of the patient although some part of the patient may be pulled inside of the bag, if the surgery is on a portion of the body that can be pulled inside the bag. Filtered air is supplied to the bag from blower-filter assembly 72 through duct 73 that is connected to an opening in end wall 66. Air travels the length of the bag and is exhausted through exhaust ports in end wall 65.

It is very important that the air in the bag be changed continuously. In one embodiment of the invention, the blower-filter assembly provided ten times the volume of the bag every minute. To maintain the bag properly inflated with an adequate flow of air through the bag, a volume of air equal to at least double the volume of the bag should be supplied to the bag every minute.

In the embodiment shown, air lock 74 is attached to end 65 of the bubble. The air lock is used to pass instruments, materials, and prostheses into and out of the bubble. It also serves as the conduit through which most of the air is exhausted from the bag.

In the embodiment shown, the air lock includes a rigid framework of angle iron connected to form rectangular end frames 75 and 76 that are held upright by struts 77 extending between the corners of the end frames. The outside of the framework is covered by the same clear, flexible plastic used for the bag except for window 78 in the top that is made of the same rigid optically transparent material used for window 67 in the top of the bag.

Figure 9:
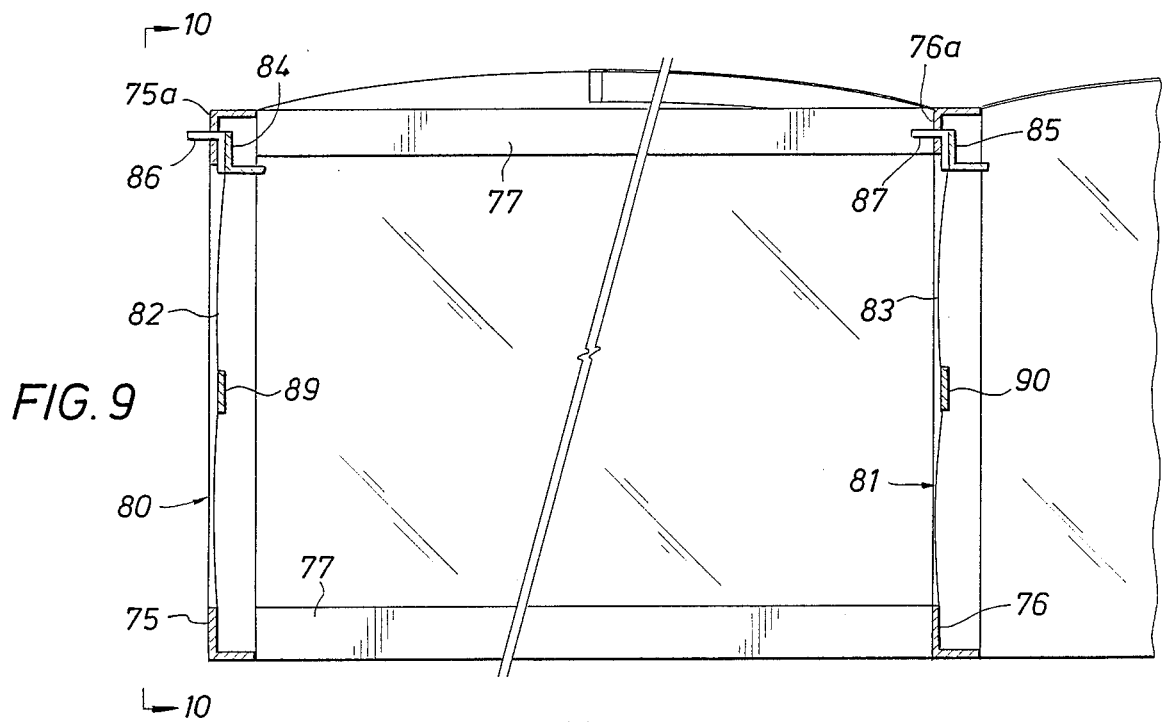
FIG. 9 is a sectional view, on an enlarged scale, taken along line 9—9 of FIG. 7.
Figure 10:
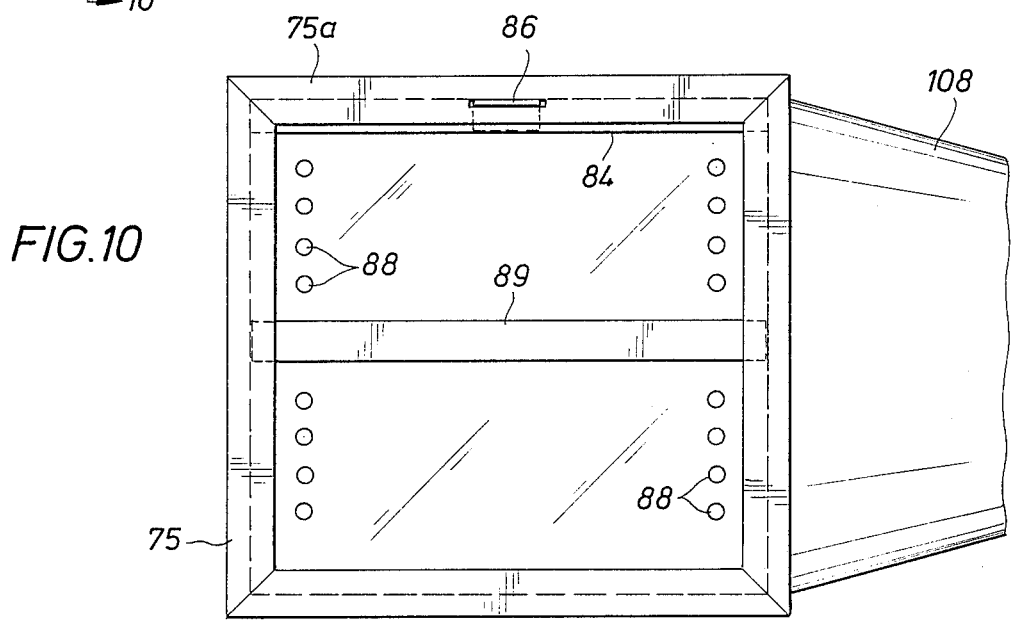
FIG. 10 is a view in elevation looking in the direction of arrows 10—10 of FIG. 9.
Figure 11:
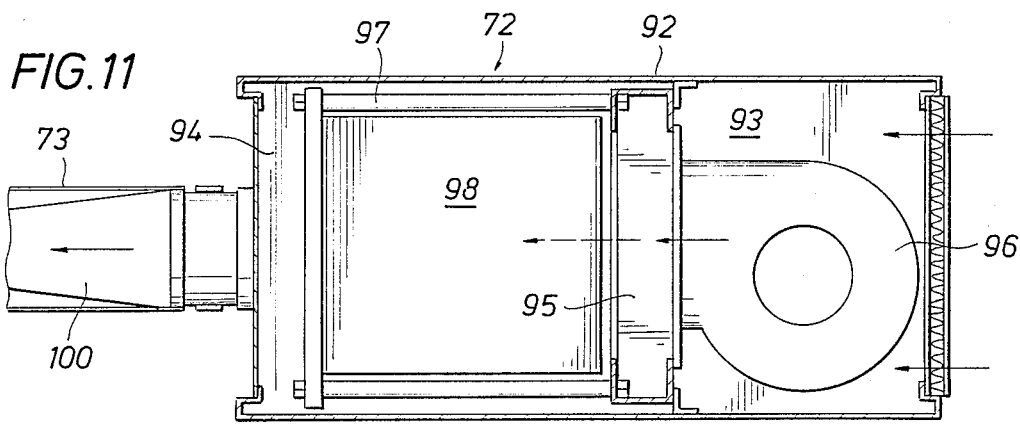
FIG. 11 is a sectional view on an enlarged scale, taken along line 10—10 of FIG. 7.

End frame 76 is connected to an opening in end wall 65 of the bag. To function as an air lock, doors or the like are located at each end, one to allow material to be moved into and out of the air lock from the outside. The other to allow material to be moved into and out of the air lock from the bag. In the embodiment shown, these door functions are provided by end flaps 80 and 81. The flaps include rectangular sheets 82 and 83 of clear, flexible plastic that are connected along the lower edge to the bottom of the end frames. The opposite sides of the flaps are connected to rigid support members 84 and 85. The flaps are held in position closing the air lock by L-shaped latch members 86 and 87 attached to the middle of the flaps opposite support members 84 and 85 and extend through slots in upper end frame members 75a and 76a, as shown in FIG. 9. Either end of the air lock can be opened by removing the latch member from the slot, allowing the flap to collapse to the bottom of the air lock.

Openings 88 are provided in the flaps to serve as exhaust ports through which air can flow out of the bag through the air lock into the operating room. It is intended for most of the air exhausted from the bag to flow through these openings. Therefore, the size and member of openings are chosen to allow the air to flow out of the bag at about the rate that air is pumped into the bag with the pressure drop across the flaps being sufficient to maintain the desired inflation pressure in the bag. Due to the pressure drop across the flaps, rigid members 89 and 90 are attached to the flaps across the middle to engage the end frames and support the flaps.

Blower-filter assembly 72 includes housing 92 that is divided into blower compartment 93 and filter compartment 94 by plenum 95. In this embodiment, the plenum is a rectangular box having openings on opposite sides Mounted on one side to pump air into the plenum is blower 96. Mounted on the other by bolts 97 is HEPA filter 98. Mounting flanges 99 support the blower, filter, and plenum in the housing. Appropriate seals are located between the blower and the plenum and the plenum and the HEPA filter to keep unfiltered air from entering filter compartment 94 and air duct 73. Should any of the seals leak, however, with the arrangement described above, since the pressure in filter compartment 94 is greater than the pressure outside housing 72 and the pressure in blower compartment 93, filtered air will leak out of filter compartment 94, but unfiltered air cannot enter the compartment and contaminate the air entering the bag.

Conical filter 100 serves the same purpose as conical filter 46 described above in connection with FIG. 5.

In this embodiment, the bag has three sleeves 102, 103, and 104 on one side and three sleeves 105, 106, and 107 on the other side. Air lock 74 has one sleeve 108. These function in the same manner as the sleeves described above in connection with the embodiment shown in FIGS. 1-5. They are constructed differently, however, being formed of four, flat triangular pieces of plastic connected at their edges to each other and the side wall of the bag.

Smaller sleeves 109 and 110 in end wall 66 allow the passage of suction and electrocautery connections to the outside of the bag. The elastic around the openings in these sleeves provides a substantially airtight seal around the arms of the surgical team and the electrical cables and pneumatic hoses extending through the sleeves In operation, the air lock can be supported by a separate table, such as table 112. This allows the air lock to be disconnected from the bag after the surgery is completed and the surgical instruments have been moved back into the air lock. It can be disconnected simply by cutting it from wall 65 leaving it intact on table 112. The bag can then be removed and the patient prepared for removal from the operating room. While this is going on, the instruments will be somewhat protected from the air in the operating room and be available should the need arise.

From the foregoing it will be seen that this invention is one well adapted to attain all of the ends and objects hereinabove set forth, together with other advantages which are obvious and which are inherent to the apparatus and structures.

It will be understood that certain features and subcombinations are of utility and may be employed without reference to other features and subcombinations. This is contemplated by and is within the scope of the claims.

Because many possible embodiments may be made of the invention without departing from the scope thereof, it is to be understood that all matter herein set forth or shown in the accompanying drawings is to be interpreted as illustrative and not in a limiting sense.

What is claimed is:

1. An isolator for providing a continuously changing contamination-free atmosphere in which a surgical procedure can be performed or equipment that is sensitive to environmental contamination can be assembled, said isolator comprising an inflatable bag having a bottom, side walls, and end walls of flexible, impervious, material, and an upper side of relatively stiff, optically transparent, material forming a window through which the inside of the isolator can be viewed, a plurality of open-ended sleeves attached to the bag through which hands for performing a surgical procedure or assembly can enter the bag, blower means for continuously supplying the bag from one end with a sufficient volume of air to maintain the pressure in the bag above atmospheric pressure and to change the air in the bag at least two times per minute, means for filtering the air before the air enters the bag and exhaust means in the opposite end of the bag to cause the air to flow through the bag from one end to the other end to restrict the flow of air out of the bag sufficiently to maintain the pressure in the bag above atmospheric pressure sufficiently to inflate the bag.

2. The isolator of claim 1 in which a portion of the bottom of the bag is made of surgical drape material for placing over the patient where the incision is to be made during a surgical procedure.

3. The isolator of claim 1 in which the end of the bag in which the exhaust means are located has an opening therein through which surgical instruments and other equipment can be moved into and out of the bag and a flap for restricting the flow of air through the opening when surgical instruments and other equipment are not being moved through the opening but which allows sufficient air to be exhausted to cause air to flow through the bag from end to end.

4. The isolator of claim 3 further provides with an open-ended chamber having an end attached to the end of the bag with the flap positioned to close the opening between the bag and the chamber and a second flap closing the other end of the chamber to form an air lock through which surgical instruments and other equipment can be moved into and out of the bag, said flaps being provided with openings through which air can be exhausted from the bag through the air lock when either or both of the flaps are closed.

5. The isolator of claim 4 in which the top of the air lock includes a section of relatively stiff, optically transparent plastic providing a window through which the instruments and equipment in the air lock can be viewed and in which the air lock is further provided with sleeve means through which the instruments and equipment in the air lock can be handled.

6. The isolator of claim 1 in which the blower means includes a housing having an interior wall that divides the housing into first and second chambers, said first chamber having an opening through which air can enter the first chamber, an air filter located in the opening to filter larger airborne contaminants including larger bacteria, dust particles, and the like from the air entering the first chamber, a blower located in the first chamber to pump air from the first chamber into the second chamber, a plenum in the second chamber into which the air from the blower is discharged, a second filter attached to the plenum to filter the remaining contaminants from the air, said plenum and second filter being spaced from the outside walls of the second chamber so that the pressure in the second chamber will be higher than the pressure in the first chamber to insure any leakage between the chambers will be filtered air flowing from the second to the first chamber, and means connecting the second chamber to the bag.

7. The isolator of claim 1 in which the window is convex in cross-section.

8. The isolator of claim 1 in which the window is V-shaped in cross-section.

9. The isolator of claim 1 further provided with a plurality of sleeve through which the arms and hands of the workers can and move into the work place, each sleeve comprising four triangular panels attached at their base to the bag and attached to each other along the sides to form a sleeve that is rectangular in cross-section.

10. The isolator of claim 1 in which a portion of the bottom of the bag is made of surgical drape material through which an incision is made during a surgical procedure, said surgical drape material being elastic to allow a body member, upon which a surgical procedure is to be performed, to be pulled into the work space through the incision in the drape that is smaller than the member to cause the stretched elastic material to tightly surround the member and reduce the chances of disease organisms entering the work space from the outside.

11. The isolator of claim 1 in which the means supplying the air include a blower, a sterile air duct through which air from the blower is supplied to the interior of the bag at a pressure at least slightly higher than atmospheric pressure, and a sterile filter located in the air duct downstream from the end of the duct to be connected to the blower so that the connection between the sterile air duct and the blower is made upstream from the sterile filter to allow any non-sterile particles or disease organisms that are introduced into the air duct when the connection is made or in the air supplied by the blower to be trapped by the filter before they enter the bag.

12. The isolator of claim 1 in which a plurality of open-ended sleeves are attached to the bag, through which the hands and arms of the workers can extend into the work space, each sleeve having elastic material encircling the sleeve adjacent its outer end to hold the sleeve tightly around an arm extending through the sleeve to reduce the flow of air from the bag between the air and the sleeve and to cause the sleeve to intussuscept as required to allow the arm to move freely into and out of the bag.

13. An isolator for reducing the chances of disease organisms entering the surgical wound of a patient during a surgical procedure, said isolator comprising an inflatable bag having side and end walls of flexible material, a lower side of flexible material, a portion of which is of an elastic surgical drape material in which an incision can be made to allow a body member upon which a surgical procedure is to be performed to be pulled into the work space and substantially isolated from the ambient conditions outside the isolator by pulling the member through the incision in the drape that is smaller than the member to cause the stretched elastic material to tightly surround the member, and an upper side portion of which is of flexible material and a portion of which is of relatively stiff, optically transparent, material through which the surgeon can view the area of the surgery, a plurality of open-ended sleeves attached to the bag through which the surgeon can extend his hands into the bag, and means for supplying the bag continuously with filtered air to inflate the bag to maintain a work space between the drape and the rigid, optically transparent, material in the upper side and exhaust means through which the filtered air can flow out of the bag continuously so that the air is changed continuously.

14. An isolator for reducing the chances of disease organisms entering the surgical wound of a patient during a surgical procedure, said isolator comprising an inflatable bag for positioning over the area of the patient when the surgery is to be performed, said bag having an upper side, a portion of which is of relatively stiff, optically transparent, material through which the surgeon can view the area of the surgery, a plurality of open-ended sleeves attached to the bag through which the surgeon can extend his hands into the bag, a blower, a sterile air duct through which air is supplied to the interior of the bag by the blower, air exhaust means through which air can flow from the bag, and a sterile filter located in the air duct downstream from the end of the duct to be connected to the blower so that the connection between the sterile air duct and the blower is made upstream from the sterile filter to allow any non-sterile particles or disease organisms that are introduced into the air duct when the connection is made or in the air supplied by the blower to be trapped by the filter before they enter the bag.

15. An isolator for reducing the chances of disease organisms entering the surgical wound of a patient during surgical procedure, said isolator comprising an inflatable bag of flexible material, a blower for supplying an air to the bag to inflate the bag, exhaust means through which air can escape from the bag to allow the air supplied by the blower to flow through the bag, means for filtering the air entering the bag, and a plurality of open-ended sleeves attached to the bag, through which the hands and arms of the surgeon and his assistants can extend into the work space, each sleeve having elastic material encircling the sleeve adjacent its outer ends to hold the sleeve tight around an arm extending through the sleeve to reduce the flow of air from the bag between the air and the sleeve and to intussuscept as required to allow the arm to which it is attached to move freely into and out of the bag.

16. An isolator for reducing the chances of disease organisms entering the surgical wound in a body member of a patient during a surgical procedure said isolator comprising an inflatable bag having side and end walls of flexible material, a lower side of flexible material, a portion of which is of a surgical drape material in which an incision can be made to allow a body member upon which a surgical procedure is to be performed to be pulled into the work space through the incision in the drape that is smaller than the member to cause the stretched elastic material to tightly surround the member and protect the body member from the environment outside the work space, and said bag having an upper side, a portion of which is of relatively stiff, optically transparent, material through which the surgeon can view the area of the surgery, a plurality of open-ended sleeves attached to the bag, through which the hands and arms of the surgeon and his assistants can extend into the work space, each sleeve having elastic material encircling the sleeve adjacent its outer ends to hold the sleeve tight around an arm extending through the sleeve to reduce the flow of air from the bag between the arm and the sleeve and to cause the sleeve to intussuscept as required to allow the arm to which it is attached to move freely into and out of the bag, exhaust means through which air can escape from the bag, and means for supplying the bag continuously with a sufficient volume of filtered air to inflate the bag to maintain a work space between the drape and the rigid, optically transparent, material in the upper side, said air supply means including a sterile air duct through which air is supplied to the interior of the bag by a blower and a sterile filter located in the air duct downstream from the end of the duct to be connected to a blower so that the connection between the sterile air duct and a blower is made upstream from the sterile filter to allow any non-sterile particles or disease organisms that are introduced into the air duct when the connection is made or in the air supplied by the blower to be trapped by the filter before they enter the bag.

17. An isolator for reducing the chances of airborne contaminants entering the surgical wound of a patient during a surgical procedure comprising an inflatable bag of flexible, impervious, material with a window in the upper side of relatively stiff, optically transparent, material through which the surgeon can view the area of the surgery, said bag being elongated having end and side walls and an inlet in one end wall, an inlet blower means for supplying the bag continuously through the inlet, means for filtering the air from the blower before the air enters the bag, and exhaust means in the opposite end wall to cause the air to flow through the bag from one end to the other with a pressure drop sufficient to inflate the bag.

18. A method of providing a continuously changing contamination-free atmosphere in which a surgical procedure can be performed by a surgeon comprising the steps of placing on the patient an inflatable bag having a bottom, side walls, and end walls of flexible, impervious, material and an upper side of relatively stiff, optically transparent material forming a window through which the inside of the bag can be viewed by the surgeon, extending the arms of the surgeon into the bag through open-ended sleeve attached to the bag and performing the surgery, continuously supplying the bag from one end with a sufficient volume of air to maintain the pressure in the bag above atmospheric and to change the air in the bag at least two times per minute, filtering the air before the air enters the bag, exhausting the air from the bag through the opposite end from where the air enters the bag, and restricting the flow of air out of the bag sufficiently to maintain sufficient pressure in the bag to keep it inflated.

* * * * *